United States Patent [19]

Finneran

[11] Patent Number: 4,669,771

[45] Date of Patent: Jun. 2, 1987

[54] CAPSULE HOLDER

[76] Inventor: James G. Finneran, 636 Jefferson Ave., Vineland, N.J. 08360

[21] Appl. No.: 838,908

[22] Filed: Mar. 12, 1986

[51] Int. Cl.⁴ .............................................. B25B 9/02
[52] U.S. Cl. ...................................... 294/99.2; 294/33
[58] Field of Search ...................... 294/99.2, 99.1, 16, 294/28, 33, 106

[56] References Cited

U.S. PATENT DOCUMENTS 4,226,459 10/1980 Natalicio ............................ 294/99.2

Primary Examiner—James B. Marbert
Attorney, Agent, or Firm—Ratner & Prestia

[57] ABSTRACT

The present invention comprises a capsule holder for loosely holding a capsule, such as a capsule containing a pharmaceutical agent, during fluid immersion testing. A plurality of resilient gripping fingers surround a space sufficiently large to receive and retain the capsule. The fingers are connected at one end by connecting arms and may be resiliently deflected outwardly to permit insertion of the capsule into the retaining space.

10 Claims, 4 Drawing Figures

CAPSULE HOLDER

BACKGROUND OF THE INVENTION

A. Field of the Invention

This invention relates to a device for holding capsules during immersion testing and, in particular, to a capsule holder wherein the capsule is loosely held by resilient fingers.

B. Background Art

In pharmaceutical and laboratory research, capsules (usually containing pharmaceutical agents) are immersed in acid solutions which simulate stomach acid to determine the dissolution characteristics of the capsule when the capsule is exposed to stomach acid. Therefore a capsule undergoing dissolution testing is retained in a device which permits fluid to freely flow to the capsule while having minimum surface contact with the capsule. The capsule holding device is preferably formed of a material which is not easily corrodible by the acid. For efficient testing of a large number of capsules, insertion of a capsule into the capsule holder should be easily performed.

For this type of immersion testing, it is known in the art to entrap capsules, for example, in a gold coated or stainless steel wire basket or in a few turns of non-corrosive wire. Nevertheless, the material holding the capsule usually corrodes over a period of time due to exposure to the acids.

It is also known generally to grip objects with devices having claws or fingers. See, for example U.S. Pat. No. 559,840—Bromley and U.S. Pat. No. 1,545,693—Phoel. Bromley discloses a plurality of pivoted jaws for retaining and handling a small object. However the handle of Bromley's tool must be rotated to open and close the jaws thereby preventing convenient insertion of the object into the tool. The tool disclosed by Phoel also may be used to grasp a small object. However the grasping device taught by Phoel grasps the object tightly and would not be suitable for immersion testing of capsules in which the capsule may be deformed or ruptured by a tightly grasping holding device thereby possible distorting dissolution resolution data.

U.S. Pat. No. 3,888,362—Fletcher et al., U.S. Pat. No. 4,260,187—Bejczy, and U.S. Pat. No. 649,785—Weinert also teach devices for grasping an object in which inconvenient mechanical manipulation is required for opening the grasping device and the jaws of the grasping device may press tightly upon the object grasped. Other patents identified to be of possible interest in a brief patentability search which was conducted for purposes of considering the patentability of the invention disclosed and claimed herein were:

U.S. Pat. No. 2,102,546: Schatz
U.S. Pat. No. 2,416,109: Terry
U.S. Pat. No. 2,827,689: Shoffner et al.
U.S. Pat. No. 3,113,799: Budnik
U.S. Pat. No. 3,640,519: Halstead
U.S. Pat. No. 3,696,490: Secunda
U.S. Pat. No. 4,439,090: Schaefer Applicant believes these patents are no more pertinent to the present invention than those discussed specifically above.

SUMMARY OF THE INVENTION

The present invention comprises a capsule holder for loosely holding a capsule, such as a capsule containing a pharmaceutical agent, during fluid immersion testing. A plurality of resilient gripping fingers surround a tapered space sufficiently large to receive and retain the capsule. The fingers are connected at one end by connecting arms and may be resiliently deflected outwardly to permit insertion of the capsule into the retaining space. The fingers are also resiliently biased toward one another to a rest position at which the distance between the fingers is adapted to prevent the capsule from passing between the fingers and out of the space during immersion. Preferably, the holder is formed of a material having a density greater than the density of water for sinking a capsule having a density less than the density of water.

DETAILED DESCRIPTION OF THE INVENTION

Figure 1:
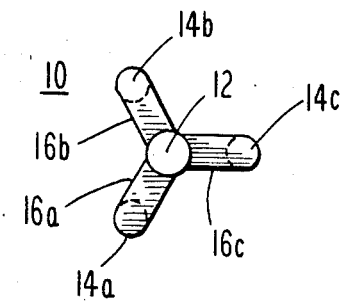
FIG. 1 is a top view of the capsule holder of the present invention.
Figure 2:
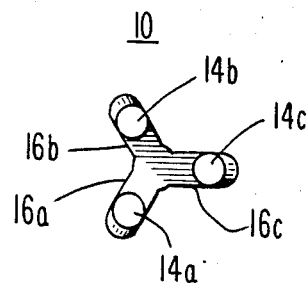
FIG. 2 is a bottom view of the capsule holder of FIG. 1.
Figure 3:
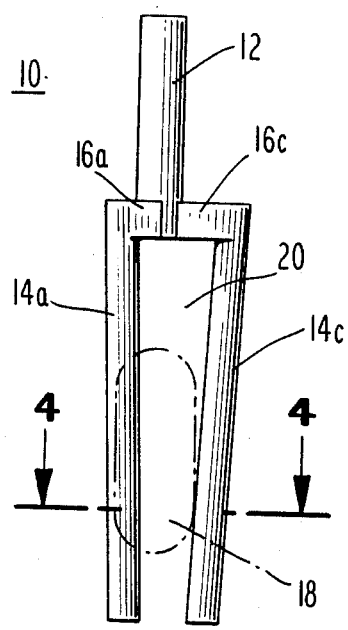
FIG. 3 is a side view of the capsule holder of FIG. 1.
Figure 4:
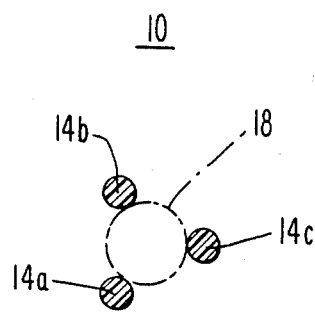
FIG. 4 is a cross-sectional view of the capsule holder of FIG. 3.

Referring now to FIGS. 1–3, there is shown capsule holder 10 of the present invention. Capsule holder 10 comprises downwardly extending resilient fingers 14a, b, c connected respectively at their upper ends to one another by connecting arms 16a, b, c, and preferably in turn to a holding means, namely, shaft 12. Resilient fingers 14a, b, c define space 20 for loosely retaining capsule 18 and may be resiliently deflected outwardly from space 20 to allow capsule 18 to be inserted into space 20. The distance between fingers 14a, b, c is adapted to prevent passage of a captive capsule 18 out of space 20 when fingers 14a, b, c are in an undeflected position.

Space 20 of capsule holder 10 is tapered by adapting fingers 14a, b, c to slant inwardly towards each other in the downward direction from connecting arms 16a, b, c to the free ends of fingers 14a, b, c. Thus space 20 has a decreasing transverse cross-sectional area in the downward direction. The transverse cross-sectional area of space 20 is adapted to be large enough to accommodate the predetermined diameter of capsule 18 in its upper region and small enough relative to the diameter of capsule 18 in its lower region for retaining capsule 18 in space 20. Thus capsule 18 may not pass between the free ends of undeflected fingers 14a, b, c because the free ends of fingers 14a, b, c are spaced a distance substantially less than the diameter of capsule 18.

In an alternate embodiment (not shown), fingers 14a, b, c may be parallel to each other rather than slanting inwardly toward each other. In this alternate embodiment, the free ends of fingers 14a, b, c may curve inwardly toward each other to retain capsule 18 within space 20.

Holder 10 is preferably formed of a plastic or other material that is resistant to acid to prevent corrosion of holder 10 due to contact with acid during immersion testing. The material of holder 10 is also chosen to provide enough resilience to permit fingers 14a, b, c to be easily spread apart for capsule insertion without damage to capsule 18.

In the preferred embodiment of capsule holder 10 three fingers, 14a, b, c, are provided. However, holder 10 may comprise more than three fingers provided the fingers are spaced apart to define and surround a space 20 for retaining capsule 18 and may be resiliently deflected outwardly to permit capsule 18 to be inserted into space 20.

Because the specific gravity of capsule 18 may be less than the specific gravity of water (which would allow capsule 18 to float in the immersion fluid), holder 10 may also serve as a capsule sinker. The material of holder 10 is therefore preferably chosen to have a density greater than that of water.

Shaft 12, at the junction of connector arms 16a, b, c, may be used for gripping and handling holder 10 and may be of any length convenient for this purpose. In an alternate embodiment (not shown), the free end of shaft 12 may be rounded rather than flat in order to conform to the shape of a dissolution vessel (not shown). Shaft 12 and arms 16a, b, c as well as fingers 14a, b, c are preferably formed as a single unitary structure.

Shaft 12 or the free ends of fingers 14a, b, c may be provided with magnets (not shown) or otherwise rendered magnetic in a known manner such as by magnetic coating or impregnation of the material of construction of holder 10 with magnetic particles. This would facilitate magnetically holding holder 10 during immersion testing and/or facilitate stirring of holder 10 with a magnetic stirrer during immersion in a fluid. Such magnets or magnetic material may be molded into capsule holder 10 or may be attached after the molding of holder 10.

While this invention has been described with reference to specific embodiments thereof, it is not limited thereto. Instead, the claims which follow are intended to be construed to encompass not only the forms and embodiments of the invention shown and described, but also such other forms and embodiments and such variants and modifications thereof as may be devised by those skilled in the art without departing from the true spirit and scope of the present invention as may be ascertained from the foregoing description and accompanying drawings.

I claim:

1. A device for loosely holding a capsule of predetermined dimension during fluid immersion testing, said device comprising:
    a plurality of resilient gripping fingers surrounding a space sufficiently large to receive said capsule therein;
    means for connecting said gripping fingers at one end of said fingers and for holding said fingers in a spaced-apart relationship at said connected end; and
    said fingers being resiliently deflectable outwardly from said space for permitting insertion of said capsule into said space and said fingers being resiliently biased toward said space to a rest position at which the distance between any two adjacent fingers is adapted to loosely retain said capsule within said space.

2. The device recited in claim 1 wherein there is further provided holding means coupled to said connecting means for handling said device.

3. The device recited in claim 1 wherein said space is tapered, the transverse cross-sectional area of said space decreasing in the direction away from said connecting means.

4. The device recited in claim 3 wherein said cross-sectional area in the region substantially near said connecting means is sufficiently large with respect to the diameter of said capsule to permit said capsule to be loosely held therein.

5. The device recited in claim 1 wherein there is provided three gripping fingers.

6. The device recited in claim 1 wherein said connecting means and said gripping fingers are formed as a unitary structure.

7. The device recited in claim 2 further comprising as said holding means a shaft coupled to said connecting means for handling said device.

8. The device recited in claim 1 wherein said connecting means and said gripping means are formed of an acid-resistant material.

9. The device recited in claim 1 wherein said connecting means and said gripping fingers are formed of a material having a specific gravity greater than the specific gravity of water.

10. The device recited in claim 1 further comprising magnetic material for rendering said device magnetic.

* * * * *